(12) United States Patent
Ihara

(10) Patent No.: US 11,327,637 B2
(45) Date of Patent: May 10, 2022

(54) INFORMATION PROCESSING SYSTEM, INFORMATION PROCESSING METHOD, AND RECORDING MEDIUM FOR UPDATING VIRTUAL AGENT USER INTERFACE

(71) Applicant: Sony Corporation, Tokyo (JP)

(72) Inventor: Keigo Ihara, Minato-ku (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 17/259,349

(22) PCT Filed: Jul. 22, 2019

(86) PCT No.: PCT/JP2019/028725
§ 371 (c)(1),
(2) Date: Jan. 11, 2021

(87) PCT Pub. No.: WO2020/022294
PCT Pub. Date: Jan. 30, 2020

(65) Prior Publication Data
US 2021/0271360 A1 Sep. 2, 2021

(30) Foreign Application Priority Data
Jul. 27, 2018 (JP) .............................. JP2018-141345

(51) Int. Cl.
*G06F 3/0484* (2022.01)
*G16H 20/60* (2018.01)
*G06F 3/16* (2006.01)

(52) U.S. Cl.
CPC ............ *G06F 3/0484* (2013.01); *G06F 3/167* (2013.01); *G16H 20/60* (2018.01)

(58) Field of Classification Search
None
See application file for complete search history.

(56) References Cited

U.S. PATENT DOCUMENTS

| 6,249,720 | B1 | 6/2001 | Kubota et al. |
| 2001/0008404 | A1 | 7/2001 | Naito |
| 2011/0230732 | A1 | 9/2011 | Edman et al. |
| 2016/0217532 | A1 | 7/2016 | Slavin |
| 2017/0039344 | A1* | 2/2017 | Bitran ................... G16H 40/63 |
| 2018/0210725 | A1* | 7/2018 | Vaindiner .............. G06F 9/451 |

FOREIGN PATENT DOCUMENTS

| JP | 11-250395 A | 9/1999 |
| JP | 11-259446 A | 9/1999 |
| JP | 2002-216026 A | 8/2002 |

(Continued)

*Primary Examiner* — Mandrita Brahmachari
(74) *Attorney, Agent, or Firm* — Oblon, McClelland, Maier & Neustadt, L.L.P.

(57) ABSTRACT

Provided are an information processing system, an information processing method, and a recording medium capable of presenting advice more effectively by updating a user interface of an agent according to a user's behavior modification with respect to the agent advice. An information processing system includes a control unit (200) that controls a user interface of an agent to be updated depending on whether a user has performed behavior modification in response to advice that the agent has presented to the user.

17 Claims, 16 Drawing Sheets

(56) References Cited

FOREIGN PATENT DOCUMENTS

| | | |
|---|---|---|
| JP | 2005-258820 A | 9/2005 |
| JP | 2006146858 A | 6/2006 |
| JP | 2010-204070 A | 9/2010 |
| JP | 2011-99747 A | 5/2011 |
| JP | 2013-509205 A | 3/2013 |
| WO | WO-2016156972 A1 | 10/2016 |

* cited by examiner

Fig. 4

| | PARAMETER DESCRIPTION | VALUE: 1 | VALUE: 2 | VALUE: 3 | VALUE: 4 | VALUE: 5 |
|---|---|---|---|---|---|---|
| UP0 | FAVORITE CHARACTER CATEGORY | FAMILY AND ACQUAINTANCE | ENTERTAINER | HISTORICAL FIGURE | FICTITIOUS PERSON | ANIMATION CHARACTER |
| UP1 | FAVORITE ENTERTAINMENT GENRE | IDOL | SINGER | ACTOR | TV ACTOR | COMEDY |
| UP2 | AFFECTED AGE | 1960S | 1970S | 1980S | 1990S | 2000S |
| UP3 | COMPATIBLE GENDER | MEN | | | | WOMAN |
| UP4 | INFLUENTIAL INTIMATE PERSON | RELATIVES | GRANDPARENTS | FRIENDS AND TEACHERS | ACQUAINTANCE | OTHERS |

Fig. 5

| PROFILE DATA | | UP0 | UP1 | UP2 | UP3 | UP4 |
|---|---|---|---|---|---|---|
| DATA 1: GENDER | | | | | | |
| | MEN | — | — | — | 5 | — |
| | WOMAN | — | — | — | 1 | — |
| DATA 2: DATE OF BIRTH | | | | | | |
| | 1950~59 | — | — | 1 | — | — |
| | 1960~69 | — | — | 2 | — | — |
| | 1970~79 | — | — | 3 | — | — |
| | 1980~89 | — | — | 4 | — | — |
| | 1990~99 | — | — | 5 | — | — |
| | 2000~09 | — | — | 5 | — | — |
| DATA 3: ADMIRED PERSON | | | | | | |
| | PARENT (FAMILY) | 1 | 0 | — | — | 1 |
| | TEACHER | 1 | 0 | — | — | 5 |
| | BOSS | 1 | 0 | — | — | 5 |
| | HISTORICAL GREAT | 3 | 0 | — | — | 0 |
| | ENTERTAINER | 2 | SEE DATA 4 | — | — | 0 |
| DATA 4: FAVORITE ENTERTAINER GENRE | | | | | | |
| | IDOL | — | 1 | — | — | — |
| | SINGER | — | 2 | — | — | — |
| | ACTOR | — | 3 | — | — | — |
| | TV ACTOR | — | 4 | — | — | — |
| | COMEDY | — | 5 | — | — | — |

Fig. 6

| | PARAMETER DESCRIPTION | VALUE: 1 | VALUE: 2 | VALUE: 3 | VALUE: 4 | VALUE: 5 |
|---|---|---|---|---|---|---|
| CP0 | CHARACTER CATEGORY | FAMILY AND ACQUAINTANCE | ENTERTAINER | HISTORICAL FIGURE | FICTITIOUS PERSON | ANIMATION CHARACTER |
| CP1 | ENTERTAINMENT GENRE | IDOL | SINGER | ACTOR | TV ACTOR/ ACTRESS | COMEDY |
| CP2 | ACTIVE YEARS | 1960S | 1970S | 1980S | 1990S | 2000S |
| CP3 | GENDER | MEN | | | | WOMAN |
| CP4 | RELATIONSHIP WITH USERS (INTIMACY) | RELATIVES | GRANDPARENTS | FRIENDS AND TEACHERS | ACQUAINTANCE | OTHERS |

CHARACTER EXAMPLE "USER'S OWN GRANDMA"

| CP0 (CHARACTER CATEGORY) | 1 (FAMILY AND ACQUAINTANCE) |
|---|---|
| CP1 (ENTERTAINMENT GENRE) | — |
| CP2 (ACTIVE YEARS) | 2 (1970S) |
| CP3 (GENDER) | 5 (WOMAN) |
| CP4 (RELATIONSHIP WITH USERS (INTIMACY)) | 2 (GRANDPARENTS) |

CHARACTER EXAMPLE 2 "ROCK SINGER"

| CP0 (CHARACTER CATEGORY) | 2 (ENTERTAINER) |
|---|---|
| CP1 (ENTERTAINMENT GENRE) | 2 (SINGER) |
| CP2 (ACTIVE YEARS) | 3 (1980S) |
| CP3 (GENDER) | 1 (MEN) |
| CP4 (RELATIONSHIP WITH USERS (INTIMACY)) | 5 (OTHERS) |

Fig. 10

|    | PARAMETER DESCRIPTION | 0 | ... | 9 |
|----|----------------------|---|-----|---|
| P0 | CHARACTER TASTE | MANGA STYLE | ... | REALISTIC |
| P1 | CHARACTER PERSONALITY | ACTIVE | ... | GENTLE |
| P2 | GENDER OF THE CHARACTER | MAN | ... | WOMAN |
| P3 | CHARACTER TONE | ALOOF | ... | FRIENDLY |

Fig. 11

| PROFILE DATA | | P0 | P1 | P2 | P3 |
|---|---|---|---|---|---|
| GENDER | | | | | |
| | MAN | — | — | 9 | — |
| | WOMAN | — | — | 0 | — |
| DATE OF BIRTH | | | | | |
| | 1950~59 | 9 | — | — | 0 |
| | 1960~69 | 7 | — | — | 2 |
| | 1970~79 | 5 | — | — | 4 |
| | 1980~89 | 4 | — | — | 5 |
| | 1990~99 | 2 | — | — | 7 |
| | 2000~09 | 0 | — | — | 9 |
| INTEREST | | | | | |
| | READING | — | 9 | — | — |
| | SPORTS | — | 2 | — | — |
| | ANIMATION | — | 4 | — | — |
| | TRAVEL | — | 3 | — | — |
| | MOVIES | — | 8 | — | — |

INFORMATION PROCESSING SYSTEM, INFORMATION PROCESSING METHOD, AND RECORDING MEDIUM FOR UPDATING VIRTUAL AGENT USER INTERFACE

TECHNICAL FIELD

The present disclosure relates to an information processing system, an information processing method, and a recording medium.

BACKGROUND ART

In recent years, an agent system that recommends contents and behaviors according to the user's question or request, or context using a smartphone, a tablet terminal, a wearable device, or a dedicated terminal such as a home agent has been known.

For example, PTL 1 below discloses a technology of changing a visual aspect of an agent character so as to correspond to a change in the tendency (user's preference based on search for a spot or a route) of the user's behavior regarding an agent character in a car navigation system. In this way, the user can immediately understand the change in his/her preference and interest.

PTL 2 below discloses a technology of changing a personality parameter of a virtual pet in accordance with accumulation of conversion between a user and the virtual pet.

PTL 3 below discloses a technology of determining the personality of an agent that communicates with a user in a car navigation system according to the user's profile (age, gender, and interest) or a surrounding environment (weather and vehicle type).

CITATION LIST

Patent Literature

[PTL 1]
　JP 2010-204070A
[PTL 2]
　JP 2002-216026A
[PTL 3]
　JP H11-259446A

SUMMARY

Technical Problem

However, the technologies disclosed in Patent Literatures described above do not take how the agent affects the user into consideration. In an agent system that presents advice to a user, it is required to present advice more effectively by taking whether the user has accepted the advice into consideration.

Therefore, the present disclosure proposes an information processing system, an information processing method, and a recording medium capable of presenting advice more effectively by updating a user interface of an agent according to a user's behavior modification with respect to the agent advice.

Solution to Problem

According to the present disclosure, an information processing system including: a control unit that controls a user interface of an agent to be updated depending on whether a user has performed behavior modification in response to advice that the agent has presented to the user is proposed.

According to the present disclosure, an information processing method for causing a processor to execute: controlling a user interface of an agent to be updated depending on whether a user has performed behavior modification in response to advice that the agent has presented to the user is proposed.

According to the present disclosure, a recording medium having a program recorded thereon, the program causing a computer to function as: a control unit that controls a user interface of an agent to be updated depending on whether a user has performed behavior modification in response to advice that the agent has presented to the user is proposed.

Advantageous Effects of Invention

As described above, according to the present disclosure, it is possible to present advice more effectively by updating a user interface of an agent according to a user's behavior modification with respect to the agent advice.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 4 is a diagram illustrating user's parameters used when determining the compatibility with a user according to the present embodiment.

FIG. 5 is a diagram illustrating an example of a relational table of user's profile information and user parameters according to the present embodiment.

FIG. 6 is a diagram illustrating character parameters used when determining the compatibility with a user according to the present embodiment.

FIG. 7 is a diagram illustrating an example of an information input screen of a private character according to the present embodiment.

FIG. 8 is a diagram illustrating an example of character parameters allocated to each character according to the present embodiment.

FIG. 10 is a diagram illustrating an example of parameters that determine a character's properties according to the present embodiment.

FIG. 11 is a diagram illustrating an example of user parameters allocated on the basis of user's profile data according to the present embodiment.

DESCRIPTION OF EMBODIMENTS

Figure 1:
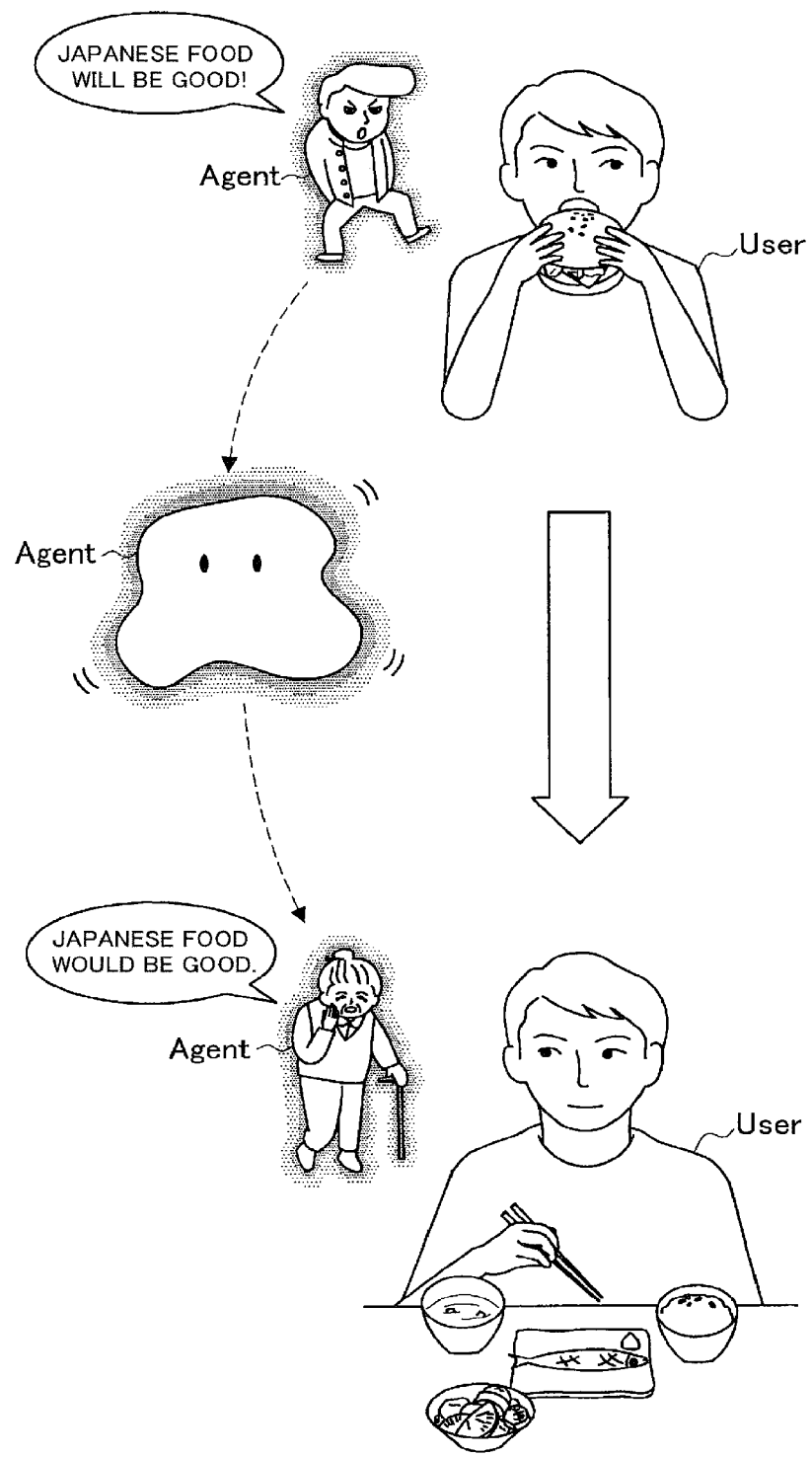
FIG. 1 is a diagram illustrating an overview of an information processing system according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.

1. Overview of information processing system according to an embodiment of present disclosure
2. Configuration example of information processing device 2
3. Operation processing
   3-1. Updating of agent character
   3-2. Updating based on stepwise adjustment of agent character
   3-3. Select agent character for respective advice services
   3-4. Updating based on appearance frequency of agent character
4. Conclusion <<1. Overview of Information Processing System According to an Embodiment of Present Disclosure>>

FIG. 1 is a diagram illustrating an overview of an information processing system according to an embodiment of the present disclosure. As illustrated in FIG. 1, an information processing system according to the present embodiment updates a user interface of an agent depending on whether a user has performed behavior modification in response to advice of the agent in an agent system that provides various pieces of information and presents advice appropriate to the user according to the user's question or request. In the present specification, the "user interface" means the appearance, the voice, the personality, or the like of an agent that performs interaction with a user.

For example, "Japanese food" which is a nutritionally balanced and healthy diet is recommended to a user as a dietary advice, if a user interface of an agent that presents the advice is a character that seems to behave badly as illustrated in the upper part of FIG. 1, the user may not accept the advice (behavior modification does not occur).

Therefore, in the information processing system according to the present embodiment, the user interface of an agent is updated depending on whether the user has accepted advice (specifically, whether behavior modification is recognized), and the user interface is changed to a (reliable) character in which the user is more likely to accept the advice, such as, for example, a character that the user likes, a character of a person that the user admires, or a character that the user sympathize with. In this way, it is possible to present advice more effectively.

For example, as described above, the agent character is updated (changed) when the user has not performed behavior modification even if a dietary advice is presented in such a character that seems to behave badly as illustrated in the upper part of FIG. 1 (for example, when the dietary habit is not modified even if a nutritionally balanced and healthy diet is recommended to a user who always eats junk food). Specifically, when the person that the user admires is a grandmother, for example, a grandmother character is selected from several agent characters and the user interface (appearance, voice, personality, or the like) of the agent is updated to the grandmother character. When advice is received from the agent of the grandmother character, it can be expected that the user is more likely to accept the advice (for example, behavior modification in dietary habit).

Here, an agent is software that autonomously supports user's behavior, provides (recommends) various pieces of information to the user, and interacts with the user and performs interaction with the user via various devices (agent devices). The agent may be a new agent system (referred to as a master system) that encourages users to change their action in order to approach problem solving from a long-term perspective, for example, as well as a general agent system that directly provides one session of a short-term response to users. Here, the "master" is the name (a master-like model) of a virtual agent that encourages users to change their action spontaneously. For example, a master system automatically generates predetermined action rules (means for solving problems in a community, predetermined value criteria (that is, values), a predetermined rhythm of life, and the like) for each specific community or user and indirectly encourages the community or user to change the action on the basis of the action rules to solve the problems of the community. That is, while the user is acting according to the words of the master, even if the user is not aware of the action rules, the problems in the community are solved without realizing the same, the user can take actions conforming to the value criteria, and the situation of the community is improved.

Figure 2:
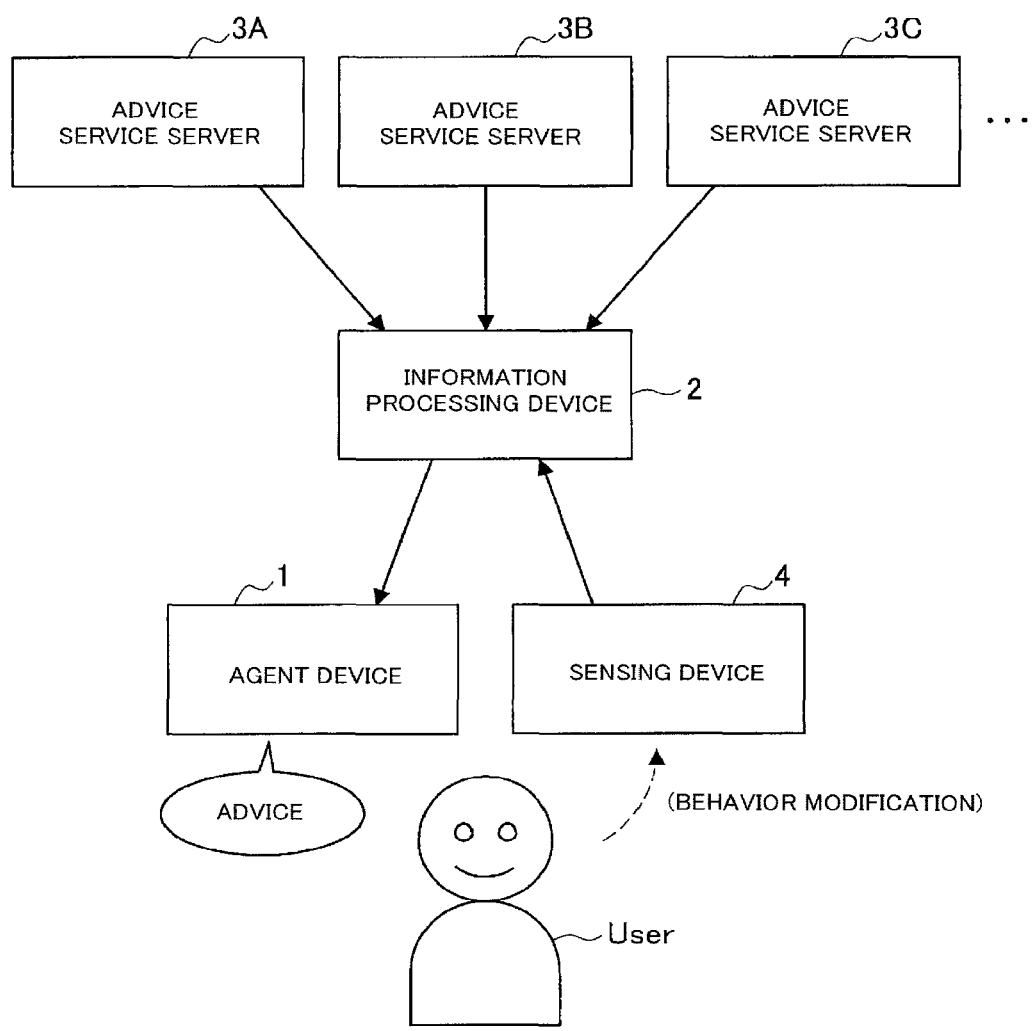
FIG. 2 is a diagram illustrating an example of an entire configuration of the information processing system according to the present embodiment.

Next, an overall configuration of the information processing system according to the present embodiment will be described with reference to FIG. 2. FIG. 2 is a diagram illustrating an example of an entire configuration of the information processing system according to the present embodiment.

As illustrated in FIG. 2, an information processing system according to the present embodiment includes an agent device 1 that functions as a user interface that presents advice from an agent to a user and an information processing device 2 that generates an agent character.

The information processing device 2 acquires advice to the user from an external advice service system (specifically, an advice service server 3) and outputs the advice to the external agent device 1. In this case, the information processing device 2 updates the agent device 1 to a user interface of a selected character agent and presents advice.

The advice service server 3 is an example of a service system that generates various pieces of information to be presented to a user such as music recommendations or dietary advice. The user can enjoy advice from a service system from which it is desired to be provided with information as advice from a predetermined agent character in the agent device 1 used by the user by subscribing to the service system. The information processing device 2 according to the present embodiment can be used as a common base (platform) that communicates with the advice service server 3 to obtain information (advice) presented to the user and performs control so that the information is presented as advice from an appropriate agent character in the agent device 1 used by the user.

The service system (the advice service server 3) may be an existing information presentation service (for example, a system that recommends contents (music, movie, event, game, and the like) and presents advice such as healthcare) and an agent service and may be a new agent system called a master system that encourages users to change their action in order to approach problem solving from a long-term perspective.

The information processing device 2 performs control involving selecting (can also generate) an agent character appropriately, updating the agent device 1 to a user interface of the selected agent character, and causing the agent character to present advice. Examples of the updated content of the user interface include changes in the appearance, voice, or personality of the agent character. Moreover, the information processing device 2 changes the agent character according to the presence of behavior modification of the user in response to advice from the agent using the agent device 1 and optimizes the user interface of the agent in the agent device 1. The presence of behavior modification of the user can be determined on the basis of various pieces of sensing data (camera data, voice data, biological information, motion sensor information, behavior history, position information, operation history, and the like) acquired from a sensing device 4, for example. The sensing device 4 may be sensors (surveillance cameras, microphones, and the like) provided around the user, may be a wearable device worn by the user, and may be provided in the agent device 1. A plurality of sensing devices 4 may be provided.

Regarding the change in the appearance of a user interface, for example, when the agent device 1 is a display device such as a smartphone, a tablet terminal, a TV device, an HMD (Head Mounted Display) or a projector device that projects an image, since the agent is displayed in a display screen or a projection region as a virtual agent, the character of the agent can be updated by switching the image. Regarding the change in appearance, when the agent device 1 is an agent robot made of a soft material and has a humanoid exterior, the exterior shape can be changed by adjusting the internal air pressure and projecting a rod-shaped arm from the inside. Moreover, when the agent robot has a white and simple shape, the projection of the texture of the agent can be switched by a projection from the outside (or inside).

Regarding output of the voice of the agent, for example, the voiceprint data of an agent character may be transmitted from the information processing device 2 to the agent device 1, and the agent device 1 speaks by synthesizing the voice from the voiceprint data using a voice synthesis engine. In this case, when updating a character, the information processing device 2 can update the voice of the agent by transmitting the voiceprint data of the character to be updated to the agent device 1.

The personality of an agent may be reflected in the tone of the wordings and endings of the agent. For example, when the personality of an agent character is updated, the information processing device 2 transmits the information on the updated personality of the agent character to the agent device 1, and the agent device 1 presents advice using the tone corresponding to the personality information. The personality information may include information on the tone.

As described above, the agent device 1 may be a display device such as a smartphone, a tablet terminal, a TV device, or an HMD, may be a projection device that projects an image, and may be a deformable agent robot. Moreover, the agent device 1 may be a wearable device such as a smart band, a smart earphone, or a smart neck (a neck-mounted speaker). Furthermore, the agent device 1 may be a home voice recognition terminal (a home terminal) (so-called voice agent device). The agent device 1 has a function (display function, a voice output function (including a voice synthesis engine), a deformation function, and the like) of restoring an agent character selected by the information processing device 2 and can present advice received from the information processing device 2 to the user as advice from a predetermined agent character.

Hereinabove, an information processing system according to an embodiment of the present disclosure has been described. The configuration of the information processing system according to the present embodiment is not limited to the example illustrated in FIG. 2. For example, the information processing device 2 may have the function of the advice service server 3, at least some steps of processing of the information processing device 2 may be performed by the agent device 1, and the agent device 1 may have all components of the information processing device 2.

Next, a specific configuration of the information processing device 2 included in the information processing system according to the present embodiment will be described with reference to the drawings.

<<2. Configuration Example of Information Processing Device 2>>

Figure 3:
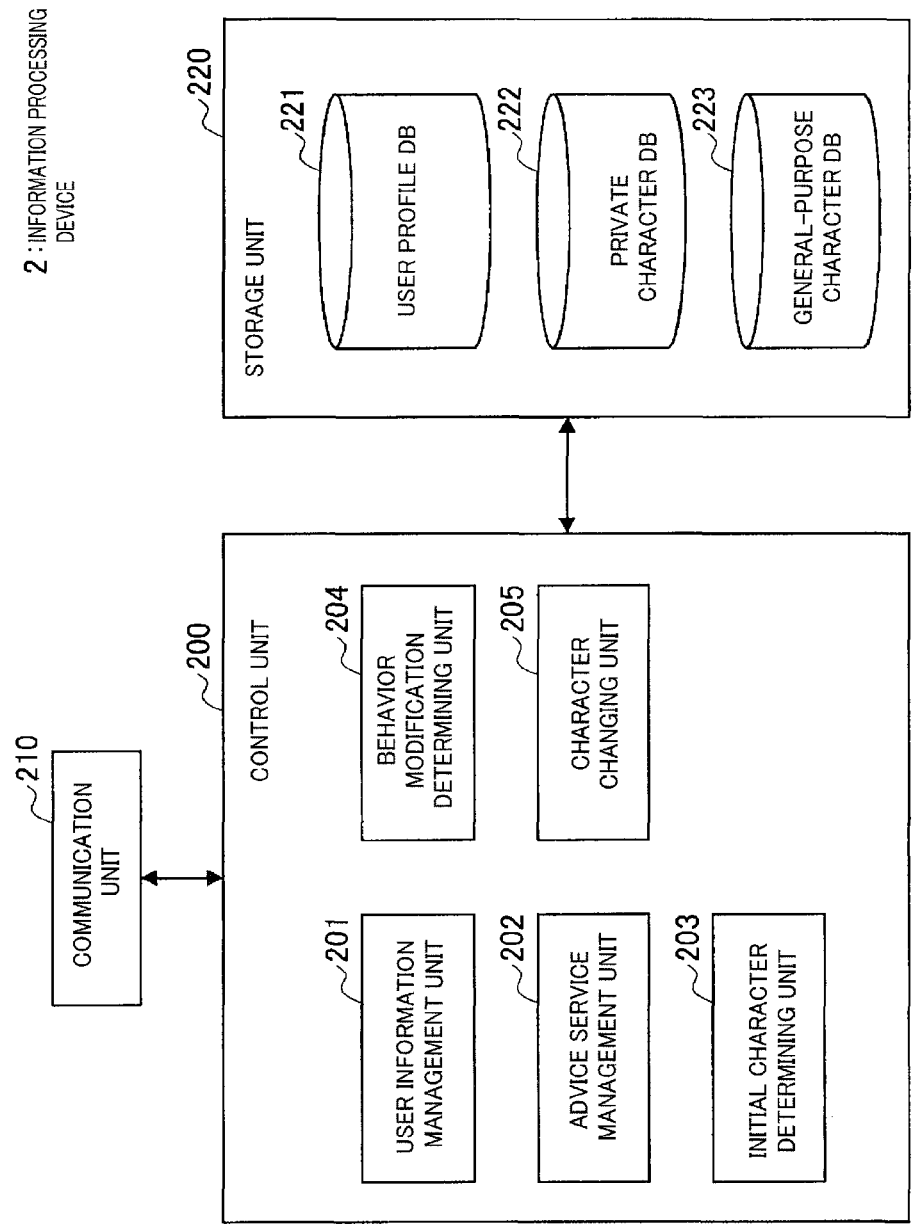
FIG. 3 is a block diagram illustrating an example of a configuration of an information processing device according to the present embodiment.

FIG. 3 is a block diagram illustrating an example of the configuration of the information processing device 2 according to the present embodiment. As illustrated in FIG. 3, the information processing device 2 includes a control unit 200, a communication unit 210, and a storage unit 220.

<2-1. Control Unit 200>

The control unit 200 functions as an arithmetic processing device and a control device and controls an overall operation of the information processing device 2 according to various programs. The control unit 200 is realized as an electronic circuit such as, for example, a CPU (central processing unit) or a microprocessor. The control unit 200 may include a ROM (read only memory) that stores programs to be used, calculation parameters, and the like and a RAM (random access memory) that temporarily stores parameters and the like that change as appropriate.

The control unit 200 according to the present embodiment may function as a user information management unit 201, an advice service management unit 202, an initial character determining unit 203, a behavior modification determining unit 204, and a character changing unit 205.

(User Information Management Unit 201)

The user information management unit 201 manages profile information and the like input by the user. The user's profile information is stored in the user profile DB 221. In the present embodiment, the character of an agent is changed on the basis of behavior modification of the user in response to advice from the agent to optimize the character (so that the user is more likely to accept the advice and effective advice can be realized). On the other hand, as a method of determining an initial character (since no feedback of behavior modification is obtained from the user), it is possible to select a character that is compatible with the personality and preference of the user by using the profile information of the user, for example. Examples of the user's profile information include gender, date of birth, admired person, and favorite entertainer genre.

(Advice Service Management Unit 202)

The advice service management unit 202 acquires advice information addressed to the user from the advice service server 3 and distributes the advice information to the agent device 1 used by the user. Information on which user has registered with which advice service server may be also managed.

(Initial Character Determining Unit 203)

The initial character determining unit 203 determines an agent character (an initial character) to be initially set to the agent device 1. The initial character determining unit 203 selects a character that is compatible with the user from agent characters (see a private character DB 222 and a general-purpose character DB 223) prepared in advance on the basis of the profile information of the user, for example, and uses the selected character as an initial character. More specifically, for example, various parameters of a character that is compatible with the user are determined on the basis of the profile information of the user, and the parameters are compared with the character parameters prepared in advance, and a character at the close coordinate is selected as the character compatible with the user.

(User Parameter; UP)

Here, parameters (UP; user parameter) of the user used when determining the compatibility with the user will be described with reference to FIG. 4. As user parameters, for example, parameters of UP0 "favorite character category" are set such that "family and acquaintance" has a value 1 (UP0; 1), "entertainer" has a value 2 (UP0; 2), "historical figure" has a value 3 (UP0; 3), "fictitious person" has a value 4 (UP0; 4), and "animation character" has a value 5 (UP0; 5). Moreover, parameters of UP1 "favorite entertainment genre" are set such that "idol" has a value 1 (UP1; 1), "singer" has a value 2 (UP1; 2), "actor" has a value 3 (UP1; 3), "TV actor" has a value 4 (UP1; 4), and "comedy" has a value 5 (UP1; 5).

According to such parameter setting, a relational table with user parameters as illustrated in FIG. 5, for example, is generated from the profile information registered by the user. As illustrated in FIG. 5, the values of parameters (UP0 to UP4) are applied according to the content input by the user in order from data 1 (gender) of the profile data. In the table, the value is not applied to the blank ("-") part. When all pieces of profile data are input, all parameters of UP0 to UP4 are filled.

(Character Parameter; CP)

The initial character determining unit 203 determines an initial character using parameters (CP; character parameter) of each agent character and parameters (UP0 to UP4) based on the profile data of the user. Here, the parameters (CP; character parameter) of the user used when determining the compatibility with the user will be described with reference to FIG. 6. As character parameters, for example, parameters of CP0 "character category" are set such that "family and acquaintance" has a value 1 (CP0; 1), "entertainer" has a value 2 (CP0; 2), "historical figure" has a value 3 (CP0; 3), "fictitious person" has a value 4 (CP0; 4), and "animation character" has a value 5 (CP0; 5). Moreover, parameters of CP1 "entertainment genre" are set such that "idol" has a value 1 (CP1; 1), "singer" has a value 2 (CP1; 2), "actor" has a value 3 (CP1; 3), "TV actor" has a value 4 (CP1; 4), and "comedy" has a value 5 (CP1; 5).

Respective items of the parameters of CP and UP have corresponding contents such as CP0; character category and UP0: favorite character category, CP1: entertainment genre, and UP1: favorite entertainment genre.

Next, an example of the character parameters prepared in advance will be described. In the present specification, a "character" is used as a general term for a shape (appearance), a voice color, or personality used when expressing an agent. Moreover, a plurality of agent characters according to the present embodiment may be prepared in advance on the system side as general-purpose characters. A general-purpose character includes generally known and public characters such as entertainers who are active on television and animation and manga characters. The general-purpose character information is stored in the general-purpose character DB 223. In addition to the general-purpose characters, the agent character according to the present embodiment may use a person close to the user, for example, a private character (user's father character or user's grandmother character) based on family, friends, acquaintances, and the like. The private character information is stored in the private character DB 222.

Figure 7:
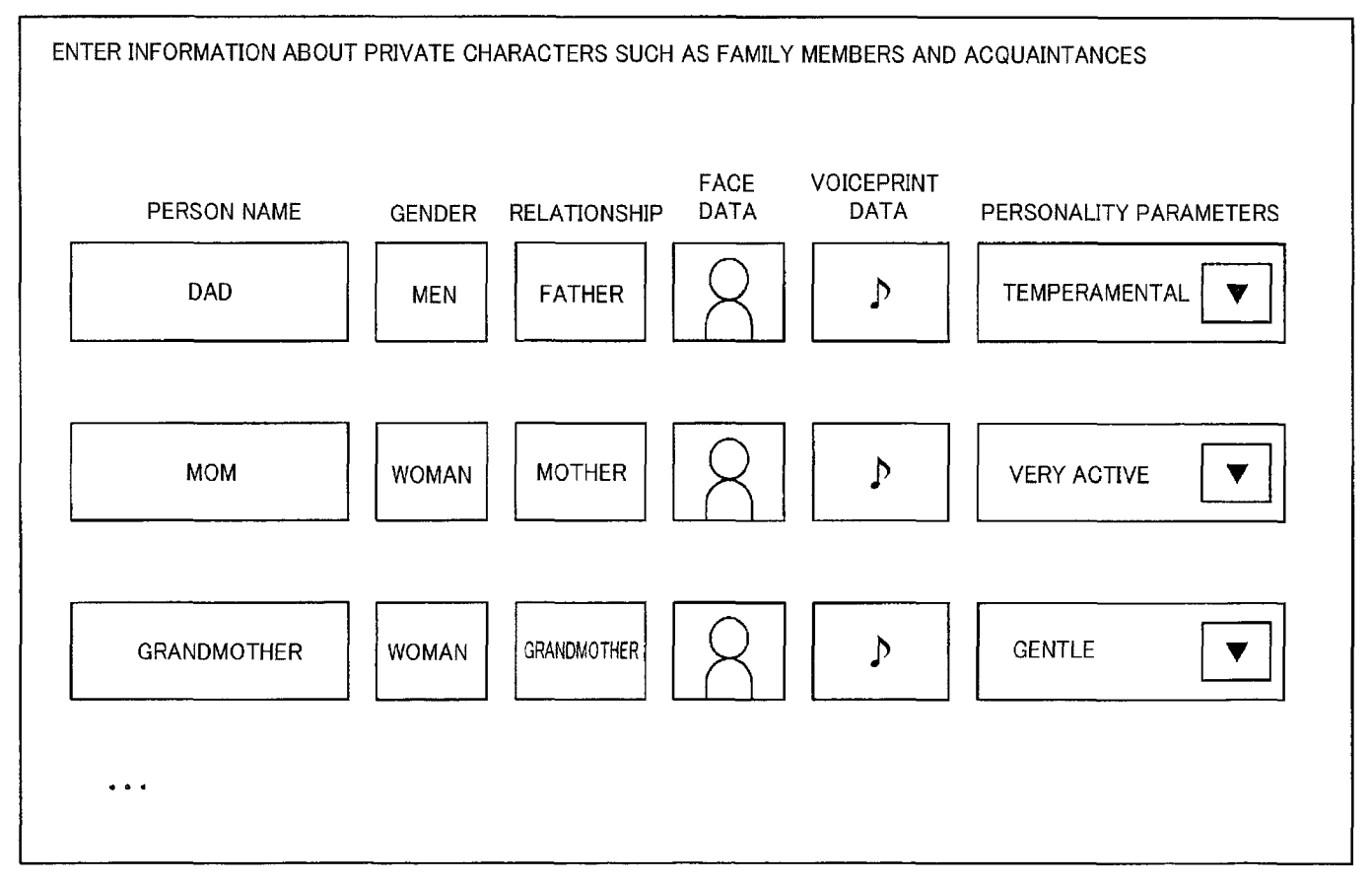

The stored character information includes appearance information (photographic images (2D and 3D data), illustrations, and the like), voice information (voiceprint data and the like), personality (personality parameters and the like), gender, age, and relationship (or intimacy or the like) with the user. It is assumed that the user himself or herself registers the information on private characters such as family and acquaintances that only the user knows. FIG. 7 is a diagram illustrating an example of a private character information input screen. As illustrated in FIG. 7, the user can input and register the information on private characters such as family and acquaintances that only the user knows.

Next, an example of character parameters (the values of CP illustrated in FIG. 6) allocated to general and private characters is illustrated in FIG. 8. CP information may be stored in each DB as information on each character.

As illustrated as character example 1 in FIG. 8, for example, values (see FIG. 6) such as "CP0; 1 (family and acquaintance)", "CP1; -(none)", "CP2; 2 (1970s)" (calculated from date of birth or the like), "CP3; 5 (woman)", "CP4; 2 (grandparents)" are allocated to the private character of "user's grandmother" on the basis of the information on the private character input by the user.

As illustrated as character example 2 in FIG. 8, for example, values (see FIG. 6) such as "CP0; 2 (entertainer)", "CP1; 2 (singer)", "CP2; 3 (1980s)", "CP3; 1 (men)", "CP4; 5 (others)" are allocated to a general-purpose character of a famous "rock singer".

(Details of Initial Character Determination)

As described above, the initial character determining unit 203 determines the initial character using the parameters (CP; character parameters) of each agent character and the parameters (UP; user parameters) based on the profile data of the user. An initial character determination method is not particularly limited, but the following method is used, for example.

For example, characters having the respective values of CP0 to CP4 are arranged at the positions of coordinates (CP0, CP1, CP2, CP3, CP4) on a multi-dimensional (5-dimensional) space having the axes of the respective parameters.

The initial character determining unit 203 calculates the distance from the coordinate (UP0, UP1, UP2, UP3, UP4) on the space to the coordinates of each character and determines a character at the closest coordinate as an initial character.

For example, the following distance calculation method may be used.

For n=0 to 4,
if $UP_n=0$,
$D_n=0$,
if $UP_n \neq 0$, $$D_n = (UP_n - CP_n)^2,$$

Distance $D = (D1 + D2 + D3 + D4)^{1/2}$ (A character of which the distance D is the smallest is selected as the initial character)

(Behavior Modification Determining Unit 204)

The behavior modification determining unit 204 determines behavior modification of the user in response to advice. For example, the behavior modification determining unit 204 can analyze various pieces of sensing data acquired from the sensing device 4 and determine behavior modification of the user. A specific example of behavior modification determination will be described later with reference to flowcharts.

(Character Changing Unit 205)

The character changing unit 205 changes (updates) the agent character (user interface) that causes interaction with the user on the agent device 1 according to the behavior modification of the user determined by the behavior modification determining unit 204. For example, if the user has not performed behavior modification even when the initial character has presented advice a predetermined number of times, the character changing unit 205 controls the agent device 1 to select another agent character having an attribute similar to the initial character from the private character DB 222 or the general-purpose character DB 223 and change the present user interface to the user interface of the selected character.

Changing (updating) of the agent character is realized by changing at least one of appearance, voice, and personality. That is, examples of the change in the agent character include change in appearance only, change in appearance and voice, change in voice only, change in voice and personality, change in appearance and personality, change in personality, and change in appearance, voice, and personality. The character changing unit 205 can continuously (repeatedly) change the character according to the user's behavior modification to optimize the agent character so that the user performs behavior modification more (that is, the user accepts advice more effectively). A specific example of changing (updating) of the agent character after the initial character is determined will be described later with reference to flowcharts.

<2-2. Communication Unit 210>

The communication unit 210 can connect to an external device via cable or wirelessly to transmit and receive data to and from the external device. The communication unit 210 can transmit and receive data to and from the advice service server 3, the agent device 1, and the sensing device 4 via a network by communicating with the network, for example, via a wired/wireless LAN (local area network), a Wi-Fi (registered trademark), Bluetooth (registered trademark), a mobile communication network (LTE (long term evolution)), or 3G (third generation mobile communication method).

<2-3. Storage Unit 220>

The storage unit 220 is realized as a ROM (read only memory) that stores programs, calculation parameters, and the like used for processing of the control unit 200 and a RAM (random access memory) that temporarily stores parameters and the like that change as appropriate.

The storage unit 220 according to the present embodiment stores the user profile DB (database) 221, the private character DB 222, and the general-purpose character DB 223, for example.

Hereinabove, the configuration of the information processing device 2 according to the present embodiment has been described in detail. The information processing device 2 may be realized as a server on a network and may be realized as an edge server of which the communication range is relatively short and which is positioned relatively close to the agent device 1. The information processing device 2 include a plurality of devices. Moreover, at least some of the components of the information processing device 2 illustrated in FIG. 3 may be provided in an external device. Furthermore, at least some of the functions of the control unit 200 of the information processing device 2 may be realized by the agent device 1. Furthermore, the functions of the control unit 200 of the information processing device 2 and the DBs of the control unit 200 may be provided in the agent device 1.

<<3. Operation Processing>>

Next, operation processing of the information processing system according to the present embodiment will be described in detail with reference to the drawings.

<3-1. Updating of Agent Character>

First, updating of the agent character according to the present embodiment will be described with reference to FIG. 9. In the information processing system according to the present embodiment, an agent to which an initial character is applied appropriately notifies the user of the content of advice generated by each advice service. Furthermore, how the user behaved in response to the notification is detected and the effect thereof is measured using various sensing devices 4 such as a camera and a microphone (detection of behavior modification).

When it is determined that there is no sufficient effect (that is, there is no behavior modification for advice) on the basis of the measurement result, the information processing device 2 reselects (updates) the agent character (that is, changes the user interface).

An example of the flow of the agent character updating processing will be described in detail with reference to FIG. 9. FIG. 9 is a flowchart illustrating an example of the flow of agent character updating processing according to the present embodiment.

Figure 9:
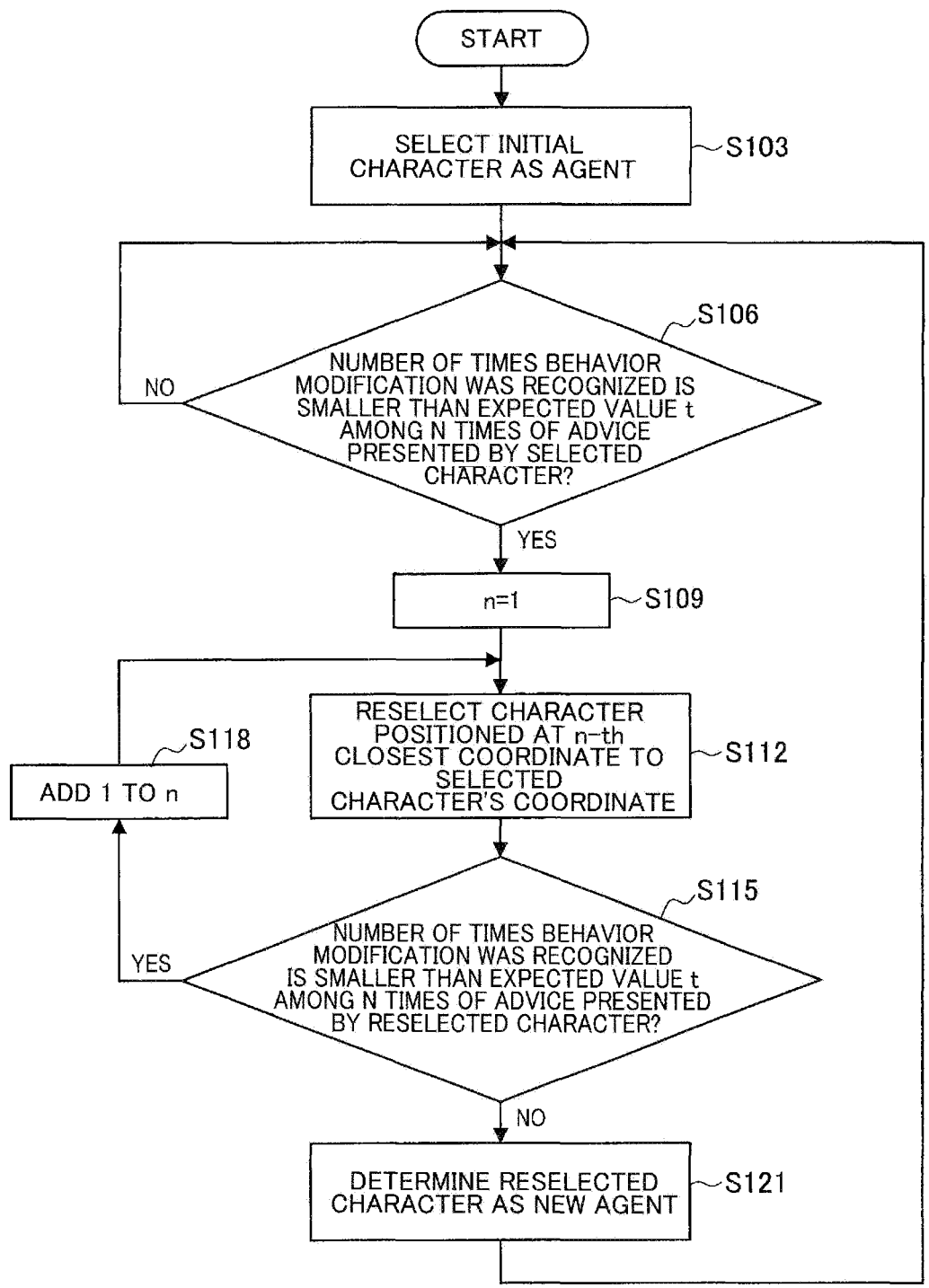
FIG. 9 is a flowchart illustrating an example of the flow of agent character updating processing according to the present embodiment.

As illustrated in FIG. 9, first, the information processing device 2 selects the initial character determined by the initial character determining unit 203 as an agent (step S103). Specifically, the information processing device 2 transmits character information such as appearance, voiceprint data, and personality of the selected initial character to the agent device 1 to cause the agent device 1 to present advice using the initial character. The advice is appropriately acquired from the advice service system by the information processing device 2 and is transmitted to the agent device 1.

Subsequently, in the information processing device 2, the behavior modification determining unit 204 determines whether the number of times behavior modification was recognized is smaller than an expected value t among N times of advice presented by the selected character (step S106). The number of times behavior modification was recognized is the number of times the user followed the advice. The behavior modification determining unit 204 detects the number of times the user has performed behavior modification in response to advice on the basis of various pieces of sensing data detected by the sensing device 4.

For example, when the agent device 1 is a home voice recognition terminal (home terminal) and a song is recommended to the user by the terminal, it is determined whether the user has requested the recommended song. For example, when songs are recommended ten times and the number of times the user has requested for playing the song is smaller than a predetermined expected threshold (for example, 7 times), the behavior modification determining unit 204 reselects (updates) the character.

For example, when the agent device 1 has presented advice on improving dietary habits, it is determined whether the user has made a menu according to the advice (whether the user has eaten according to the advice). For example, when advice on a menu is presented to the user when picking a meal and the number of times the user picked a meal according to the advice among ten meals is smaller than a predetermined expected threshold (for example, 7 times), the behavior modification determining unit 204 reselects (updates) the character. What kind of meal the user has picked may be text-input by the user himself or herself, for example. The user may take the picture of the food using the camera of the agent device 1 and the agent device 1 may determine the menu through image analysis. Furthermore, in case of IT-managed companies or school cafeterias, the food menu taken by the user may be determined on the basis of the settlement data of the user.

Subsequently, when the number of times behavior modification was recognized is smaller than the expected value t (step S106: Yes), the information processing device 2 set n=1 (step S109), and the character changing unit 205 reselects a character (the allocated CP) at the n-th closest coordinate to the coordinate to the selected character (in this case, the initial character) (step S112).

Subsequently, the information processing device 2 determines whether the number of times behavior modification was recognized is smaller than the expected value t among N times of advice presented by the reselected character in the agent device 1 (step S115).

When the number of times behavior modification was recognized is not smaller than the expected value t (step S115: No), the information processing device 2 determines the reselected character as a new agent (step S121).

On the other hand, when the number of times behavior modification was recognized is smaller than the expected value t (step S115: Yes), the character changing unit 205 adds 1 to n (step S118) and selects the character at the n-th closest coordinate again (step S112).

By repeating steps S112 to S118, it is possible to set a character from the initial character in a stepwise manner and update (optimize) the character to a character in which the effect of advice is high for the user (that is, the user is more likely to perform behavior modification (accept the advice)).

By performing the processes subsequent to step S106 even after a new agent is determined in step S121, it is possible to optimize the agent character continuously.

In the present embodiment, whether behavior modification has been performed may be determined on the basis of the number of times (ratio) behavior modification was recognized while the same advice was repeatedly presented by the same agent character. The same advice may not necessarily be presented continuously, and the advice may be mixed with other advice and presented a predetermined number of times in a certain period.

For example, when the user does a bad habit of "nail biting", the information processing device 2 may notify the user of advice for breaking the habit using the agent character over a day. The information processing device 2 may determine that the advice presented by the character was effective when the percentage (the percentage of behavior modification occurred) that the advice was effective (the user stopped the behavior according to the advice) exceeds 70%.

The repeated advices are not limited to the advices with exactly the same content, and may be advices of the same genre or from the common viewpoint (that is, advices of a common higher category).

For example, when the user does behaviors judged as bad habits such as "fidgeting" or "tongue clicking" as well as "nail biting", the information processing device 2 may repeatedly present advice for breaking the behaviors using the same agent character. Whether each of "advices on bad habits" was effective (the habits are stopped) is recorded continuously. When the number of times advice was presented reaches 10 times and the number of times the advice was effective (the user stopped the behavior according to the advice) exceeds 7 times, for example, the information processing device 2 determines that the advice presented by the character was effective.

For example, in the case of music recommendation, without being limited to repeating recommendation of the same music, the information processing device 2 recommends a music of the same artist or the same genre to the user using the same agent character on the agent device 1 repeatedly a predetermined number of times. The information processing device 2 determines whether the advice presented by the character was effective on the basis of the number of times (the number of times the recommendation was effective) the user has requested for playing the recommended music with respect to a predetermined number of times (or a predetermined period) of recommendation.

Hereinabove, an example of the operation processing according to the present embodiment has been described. The operation processing illustrated in FIG. 9 is an example, and the present disclosure is not limited to the example illustrated in FIG. 9.

<3-2. Updating Based on Stepwise Adjustment of Agent Character>

Regarding an agent character selection method, although the above-described embodiment uses a method of setting a plurality of characters in advance, discretely arranging the characters on a multi-dimensional space formed from parameters (CP; character parameters) that determine the properties of the characters, and selecting a character on the basis of a profile data or behavior modification of the user. However, the present disclosure is not limited thereto.

For example, rather than selecting one from unique characters, a method of adjusting the parameters of a character in a stepwise manner and searching for an optimal character may be used. In this case, the information processing device 2 can sequentially set an agent character of which at least one of the appearance, voice, and personality is different from that of the agent character in a stepwise manner. An example of parameters that determine the properties of a character is defined as illustrated in FIG. 10. FIG. 10 is a diagram illustrating an example of parameters that determine the properties of a character according to the present embodiment.

As illustrated in FIG. 10, a value in ten steps, for example, from "manga style" to "realistic" can be set as "P0: character taste", for example. Similarly, a value in ten steps, for example, from "active" to "gentle" can be set as "P1: character personality".

In this manner, parameters that determine the properties of a character are prepared in advance in a stepwise manner. Although not illustrated in FIG. 10, the stepwise parameters of voice (voiceprint data) may be defined in this manner. Stepwise parameters of voiceprint data, for example, may be set from "high voice (cute voice, youthful voice, restless voice, and the like)" to "low voice (heavy voice, calm voice, hoarse voice, and the like)" and from "loud voice" to "quiet voice". Moreover, "quick tongue to slow tongue" and "dialect to standard language" may be included in stepwise parameters of personality (tone).

In the present embodiment, as an example, the parameters of the character parameters CP0 to CP4 are determined in ten steps of 0 to 9. The user parameters (UP) allocated on the basis of the profile data of the user can be also set in ten steps as illustrated in FIG. 11.

FIG. 11 is a diagram illustrating an example of user parameters allocated on the basis of the profile data of the user. The initial character determining unit 203 can determine an initial character on the basis of the parameters (UP) allocated on the basis of the profile data registered for the user. For example, among the 10-step values of the user parameters illustrated in FIG. 10, a character in which a value close to the value of UP allocated on the basis of the profile of a target user is used as the setting value of P0 to P3 is set as an initial character.

The information processing device 2 can update the initial character in the following manner using the stepwise parameters by referring to the behavior modification of the user.

Figure 12:
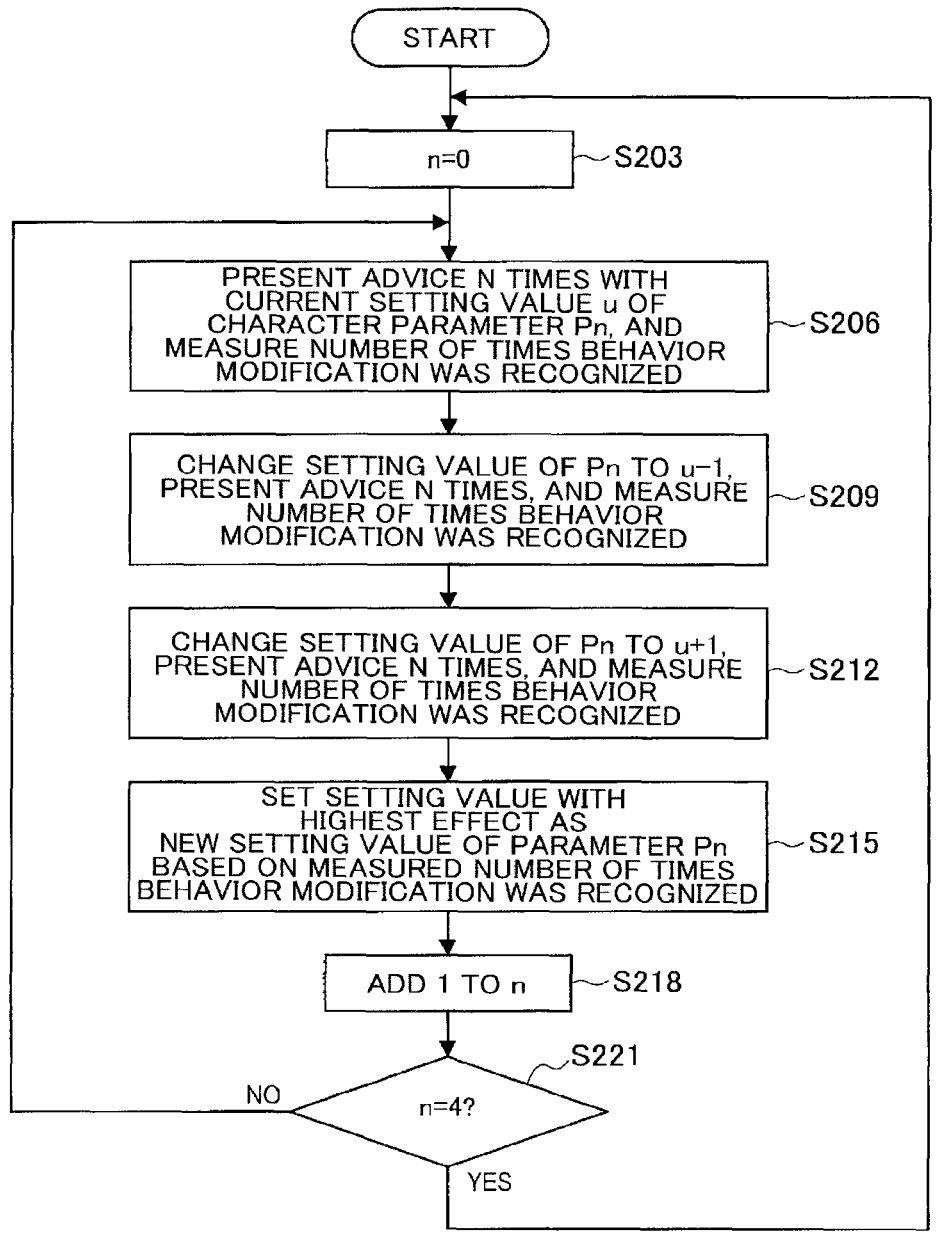
FIG. 12 is a flowchart illustrating an example of the flow of updating processing using stepwise parameters of an agent character according to the present embodiment.

FIG. 12 is a flowchart illustrating an example of the flow of updating processing using the stepwise parameters of the agent character according to the present embodiment.

As illustrated in FIG. 12, first, the information processing device 2 resets n=0 (step S203), presents advice N times using the current setting value u (for example, any one of the values 0 to 9 of the stepwise parameter illustrated in FIG. 10) of the character parameter Pn (for example, any one of P0 to P3 illustrated in FIG. 10) and measures the number of times behavior modification was recognized (step S206).

Subsequently, the information processing device 2 changes the setting value to u−1 for the same parameter Pn, presents advice N times, and measures the number of times behavior modification was recognized (step S209).

Subsequently, the information processing device 2 changes the setting value to u+1 for the same parameter Pn, presents advice N times, and measures the number of times behavior modification was recognized (step S212).

Subsequently, the information processing device 2 sets a setting value which was most effective as a new setting value of the parameter Pn on the basis of the measured number of times behavior modification was recognized (step S215).

Subsequently, the information processing device 2 adds 1 to n (step S218) and repeats steps S206 to S218 until n=4 (in this example, since there are parameters P0 to P3 as illustrated in FIG. 10) (step S221).

In this way, by testing the stepwise values before and after the current setting value of each parameter, it is possible to gradually transform the agent to a character with a higher effect of accepting advice. That is, the information processing device 2 can optimize at least one of the appearance, voice, and personality of the agent character.

(Infinite Stepwise Updating of Agent Character)

In the above-described example, for example, a method of selecting one from a plurality of characters prepared in advance and a method of selecting and setting the value of a character parameter from values of a finite number of steps such as ten steps have been described. However, the present disclosure is not limited thereto.

The present disclosure is not limited to a method of selecting a character in which "behavior modification is recognized most apparently" from a finite number of characters, but the shape of a character may be changed continuously in a form of interpolating the finite number of characters. By allowing the user to select a character at an arbitrary position on a continuous line, it is possible to change the character in an infinite number of steps and select a more optimal character.

For example, creation of continuous change in a shape can be realized using a path framework method for interpolation and a machine learning method such as GAN (Generative Adversarial Network). Moreover, when a machine learning method such as GAN is used, the same algorithm can be applied to the voice (voice color) of a character as well as the shape of a character.

Figure 13:
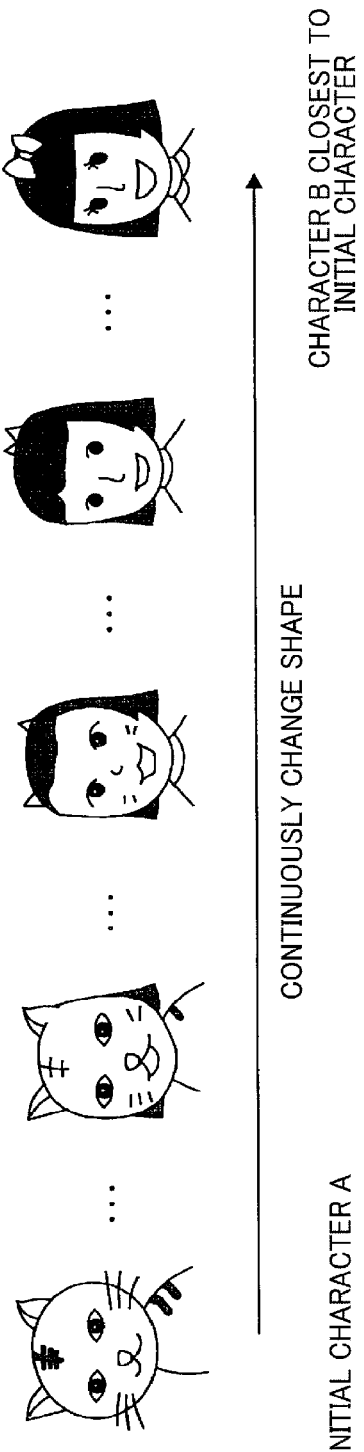
FIG. 13 is a diagram illustrating a case in which a character shape is changed infinitely stepwise to be updated to an optimal character according to the present embodiment.

In this way, for example, as illustrated in FIG. 13, the shape of a character can be continuously changed from an initial character (character A) to a character (character B) closest to the initial character and an arbitrary shape can be selected.

Figure 14:
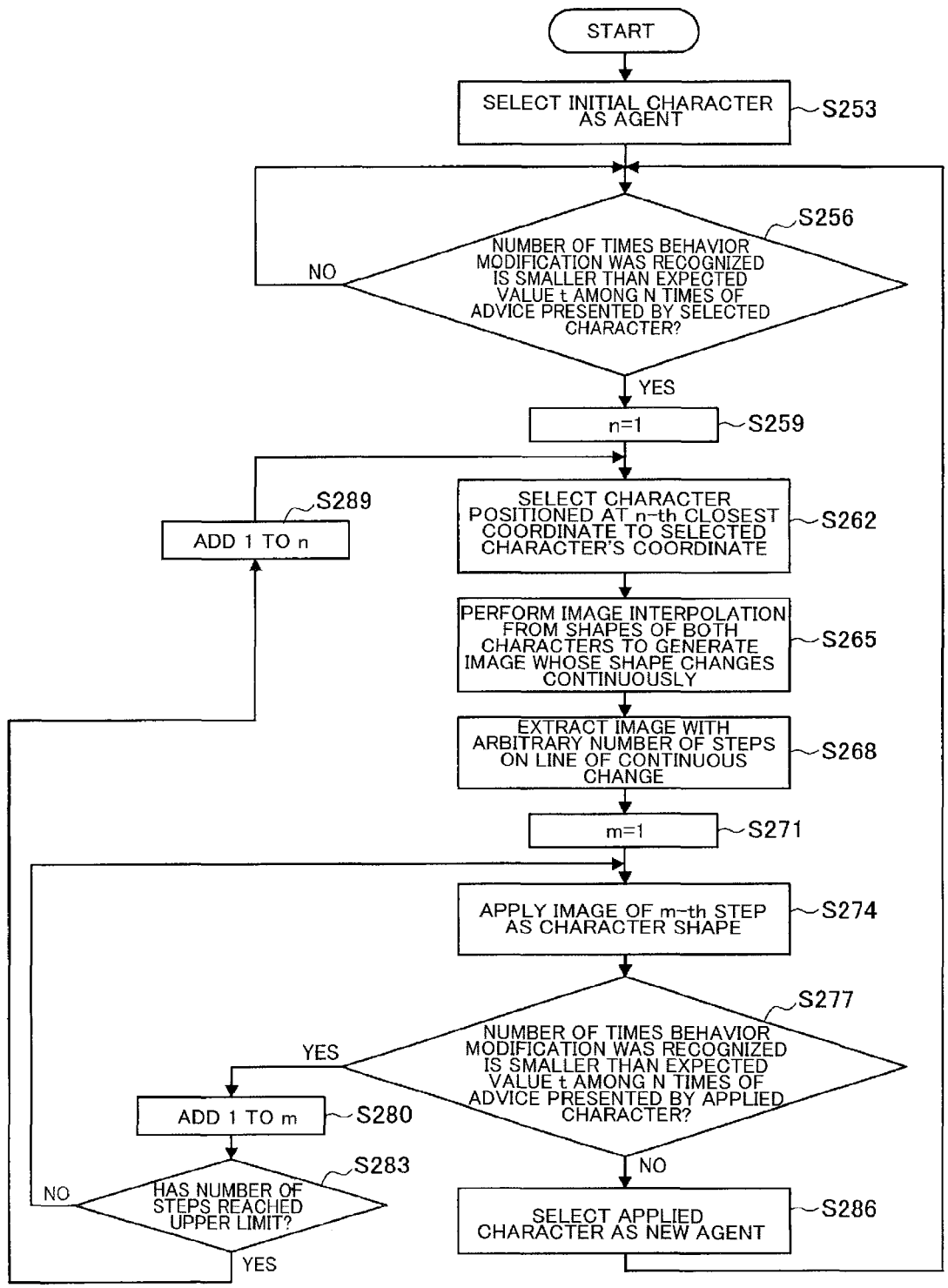
FIG. 14 is a flowchart illustrating an example of the flow of updating processing using an infinite stepwise change of an agent character according to the present embodiment.

Hereinafter, detailed description will be provided with reference to FIG. 14. FIG. 14 is a flowchart illustrating an example of the flow of updating processing using an infinite stepwise change of an agent character according to the present embodiment.

As illustrated in FIG. 14, first, the initial character determining unit 203 of the information processing device 2 selects an initial character as an agent (step S253). Regarding selection of the initial character, for example, as described above with reference to FIGS. 4 to 8, a character of which the distance D is the smallest on a multi-dimensional (5-dimensional) space having the axes of the parameters is determined as the initial character using the parameters (CP) of each agent character and the parameters (UP) based on the profile data of the user.

Subsequently, the behavior modification determining unit 204 of the information processing device 2 determines whether the number of times behavior modification was recognized is smaller than the expected value t among N times of advice presented by the selected character (step S256).

Subsequently, when the number of times is smaller than the expected value t (step S256: Yes), the character changing unit 205 of the information processing device 2 sets n=1 (step S259) and selects a character at the n-th closest coordinate to the coordinate of the selected character (on the multi-dimensional space of the respective parameters) (step S262).

Subsequently, the character changing unit 205 of the information processing device 2 performs image interpolation using the shapes of both characters to generate an image of which the shape changes continuously (so-called image morphing) (step S265) and extracts an image with an arbitrary number of steps on the line of continuous change (step S268).

Subsequently, the character changing unit 205 of the information processing device 2 sets m=1 (step S271) and applies the image of the m-th step as the shape of the character (step S274).

Subsequently, the character changing unit 205 of the information processing device 2 determines whether the number of times behavior modification was recognized is smaller than the expected value t among N times of advice presented by the applied character (step S277).

Subsequently, when the number of times is smaller than the expected value t (step S277: Yes), the character changing unit 205 of the information processing device 2 adds 1 to m (step S280) and repeats steps S274 to S280 until the number of steps reaches the upper limit (step S283).

When the number of times reaches the expected value t or larger (step S277: No), the character changing unit 205 of the information processing device 2 selects the applied character as a new agent (step S286).

In this manner, it is possible to generate an image of which the shape changes continuously and select an arbitrary image as an agent character.

In this example, the change in a character shape has been described. However, the present disclosure is not limited thereto. Similarly, for other parameters such as the voice quality (voiceprint data) and the personality (tone) of the character, pieces of data in which the parameter is changed continuously can be generated and an arbitrary data can be selected as the agent character.

<3-3. Select Agent Character for Respective Advice Services>

In the above-described embodiment, although the same agent character is selected regardless of the content of advice, the present disclosure is not limited thereto and a more effective character may be selected for respective advice services.

For example, the information processing device 2 may determine behavior modification of a user with respect to music recommendation and dietary advice and selectively use an optimal character (having a higher effect of accepting advice) for a music recommendation advice service and a dietary advice service according to the determination result of the behavior modification.

In this way, for example, in the case of music recommendation, since a young and good-looking character of the opposite gender is easily accepted by the user and is more effective, the user interface is changed to the corresponding character to present advice. Moreover, in the case of dietary advice, since the character of the familiar user's own grandmother is easily accepted by the user, the user interface is changed to the character to present advice.

<3-4. Updating Based on Appearance Frequency of Agent Character>

The information processing system according to the present disclosure may use a method of setting an appearance frequency (probability) of each character and changing (updating) the agent character on the basis of the appearance frequency.

Figure 15:
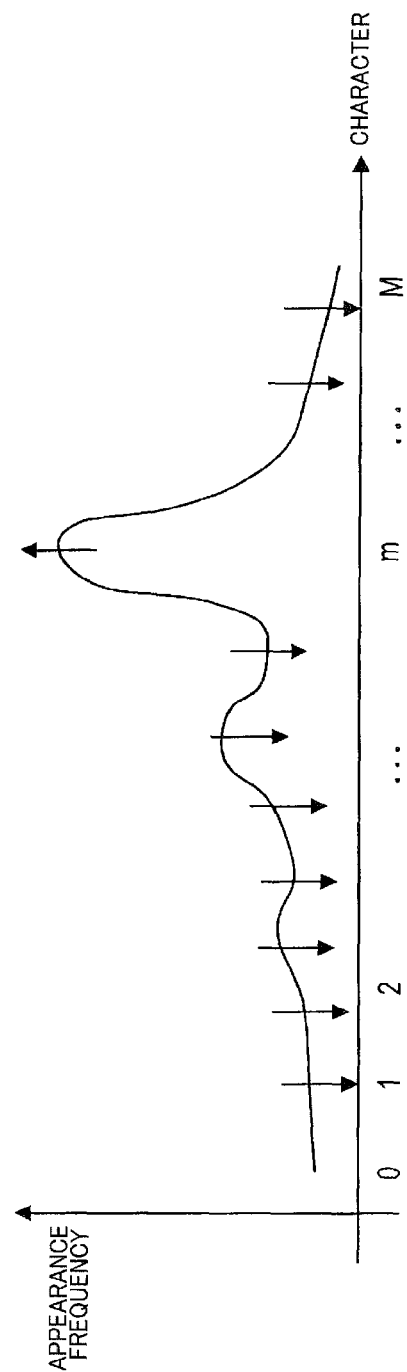
FIG. 15 is a diagram illustrating an example of an appearance frequency (probability) set to each character according to the present embodiment.

The information processing device 2 sets an appearance frequency (probability) of each of all characters (for example, a total of M) prepared in advance. Here, an example of the appearance frequency (probability) set to each character is illustrated in FIG. 15. All characters appear according to the set appearance frequencies.

In the above-described embodiment, an operation of selecting one character that is optimal at that time point, performing evaluation using the selected character repeatedly (for example, N times) for a predetermined period, and then, reselecting (updating) the character is performed repeatedly. However, in the present embodiment, a character appears on the basis of an appearance frequency when presenting advice and evaluation can be performed. For example, when a certain character m appears and presents certain advice to the user, and the user performs behavior modification in response to the advice, as illustrated in FIG. 15, the information processing device 2 performs adjustment (reflection of evaluation) in such a way that the appearance frequency of the character m is raised and the appearance frequencies of the other characters are lowered.

In this way, it is possible to reflect evaluation on all characters while showing various characters on the basis of the appearance frequency (probability) and increase the appearance frequency of a character that the user is likely to accept more efficiently.

Figure 16:
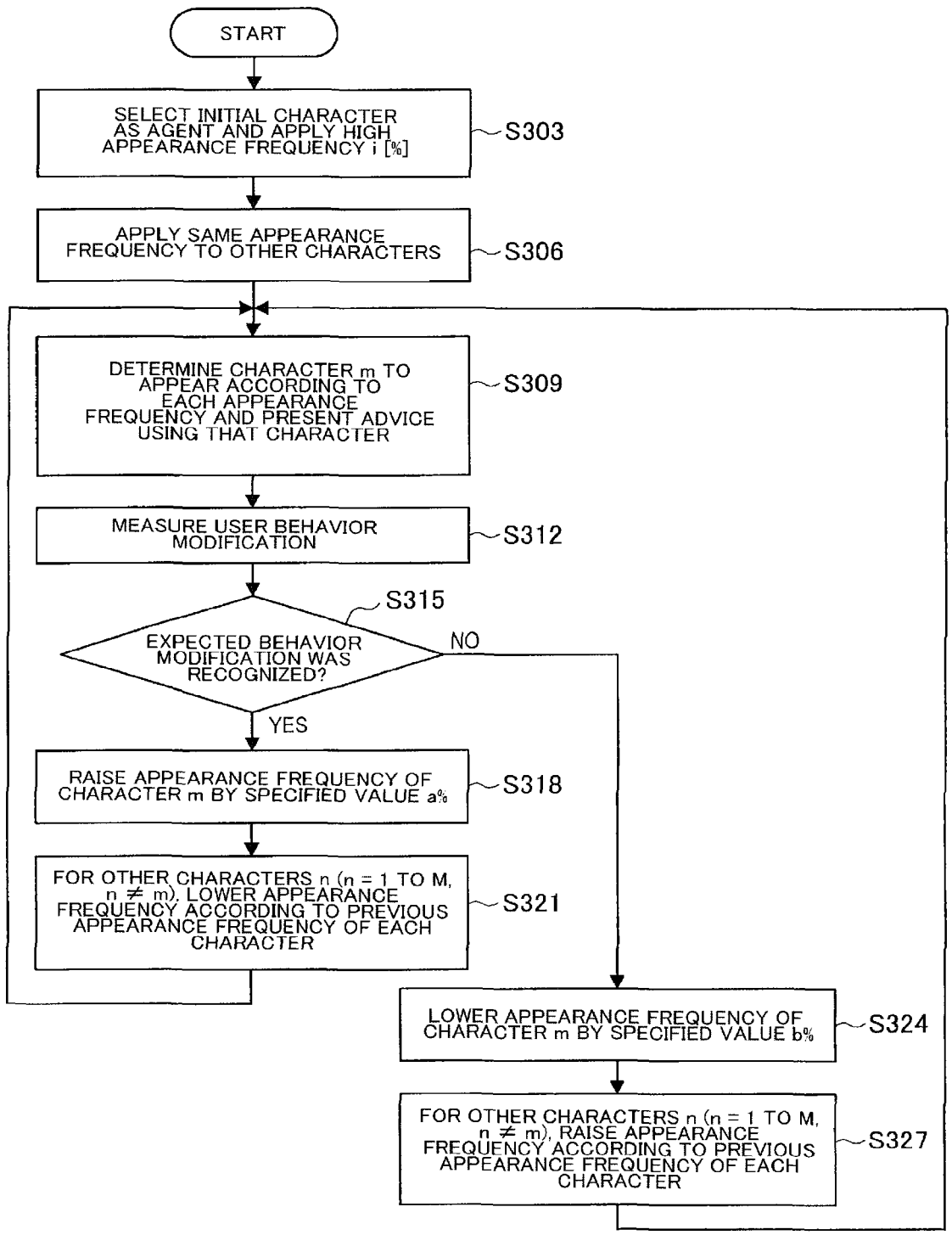
FIG. 16 is a flowchart illustrating an example of the flow of operations of agent character updating processing based on an appearance frequency of each character according to the present embodiment.

Hereinafter, detailed description will be provided with reference to FIG. 16. FIG. 16 is a flowchart illustrating an example of the flow of an operation of agent character updating processing based on the appearance frequency of each character according to the present embodiment.

As illustrated in FIG. 16, first, the initial character determining unit 203 of the information processing device 2 selects an initial character as an agent and applies a high appearance frequency i [%] (for example, 70%) (step S303).

Subsequently, the initial character determining unit 203 of the information processing device 2 applies the same appearance frequency to characters other than the character selected as the initial character (step S306). For example, when the total number of characters is M, an appearance frequency of $(100-i)/(M-1)[\%]$ is applied to characters other than the initial character (for example, if M=31, $(100-70)/(31-1)=1\%$).

Subsequently, the character changing unit 205 of the information processing device 2 determines a character m to appear according to the appearance frequency of each character and presents advice to the user using the determined character m in the agent device 1 (step S309). This processing may be performed when it is necessary to acquire, by the information processing device 2, advice to be addressed to the user from the advice service and present the advice to the user.

Subsequently, the behavior modification determining unit 204 of the information processing device 2 acquires sensing data from the sensing device 4 and measures the behavior modification of the user (step S312).

Subsequently, the behavior modification determining unit 204 of the information processing device 2 determines whether expected behavior modification was recognized (the user followed the advice) in response to the advice presented by the agent character (step S315).

Subsequently, when expected behavior modification was recognized (step S315: Yes), the character changing unit 205 of the information processing device 2 raises the appearance frequency of the character m by a specified value a % (step S318). For example, when the previous appearance frequency of the character m is Qm, a new appearance frequency Qm' is $Qm'=(1+a/100)*Qm$.

For example, when the specified value is 10%, and Qm is 70%, the new appearance frequency Qm' is 77%.

Subsequently, the character changing unit 205 of the information processing device 2 lowers the appearance frequency of the other character n (n=1 to M, n≠m) according to the previous appearance frequency of each character (step S321). For example, when the previous appearance frequency of a character n is Qn, the new appearance frequency Qn' is $Qn'=Qn-(a*Qm/100)*(Qn/(100-Qm))$.

For example, the increase of 7% of the appearance frequency of the character m is distributed according to the appearance frequencies of the other thirty characters (when the total number M is 31, the number of characters n other than the character m is 30), and the appearance frequencies of the other characters are lowered by the distributed increase.

On the other hand, when the expected behavior modification was not recognized (step S315: No), the character changing unit 205 of the information processing device 2 lowers the appearance frequency of the character m by a specified value b % (step S324). For example, when the previous appearance frequency of the character m is Qm, the new appearance frequency Qm' is $Qm'=(1-b/100)*Qm$.

For example, when the specified value is 20% and Qm is 70%, the new appearance frequency Qm' is 56%.

The character changing unit 205 of the information processing device 2 raises the appearance frequency of the other character n (n=1 to M, n≠m) according to the previous appearance frequency of each character (step S327). For example, when the previous appearance frequency of a character n is Qn, the new appearance frequency Qn' is Qn'=Qn+(b*Qm/100)*(Qn/(100−Qm)).

For example, the decrease of 14% of the appearance frequency of the character m is distributed according to the appearance frequencies of the other thirty characters and the appearance frequencies of the other characters are raised by the distributed decrease.

<<4. Conclusion>>

As described above, in the information processing system according to the embodiment of the present disclosure, it is possible to present advice more effectively by updating a user interface of an agent according to a user's behavior modification with respect to the agent's advice.

While the preferred embodiments of the present disclosure have been described above with reference to the accompanying drawings, the present disclosure is not limited to the above examples. A person skilled in the art may find various alterations and modifications within the scope of the technical idea described in the claims, and it should be understood that they will naturally come under the technical scope of the present disclosure.

For example, a computer program for causing hardware such as a CPU, a ROM, and a RAM included in the information processing device 2 to perform the functions of the information processing device 2. A computer-readable storage medium having the computer program stored therein is also provided.

Further, the effects described in this specification are merely illustrative or exemplified effects, and are not limitative. That is, with or in the place of the above effects, the technology according to the present disclosure may achieve other effects that are clear to those skilled in the art based on the description of this specification.

Note that, the following configurations also fall within the technical scope of the present disclosure.

(1)

An information processing system including: a control unit that controls a user interface of an agent to be updated depending on whether a user has performed behavior modification in response to advice that the agent has presented to the user.

(2)

The information processing system according to (1), wherein the control unit optimizes the user interface of the agent such that the user performs behavior modification more in response to the advice.

(3)

The information processing system according to (2), wherein when behavior modification of the user in response to the advice is lower than a predetermined expected value, the control unit changes the agent to another agent of which at least one of the appearance, voice, and personality of the agent is different from that of the agent.

(4)

The information processing system according to (2) or (3), wherein the control unit is capable of sequentially setting an agent of which at least one of the appearance, voice, and personality of the agent is different from that of the agent in a stepwise manner, and detects a result of behavior modification of the user when each agent presents advice to the user, and optimizes at least one of the appearance, voice, and personality of the agent on the basis of the detection result.

(5)

The information processing system according to any one of (2) to (4), wherein the control unit optimizes a user interface of the agent for each type of the advice.

(6)

The information processing system according to (3) or (4), wherein the control unit optimizes the agent by integrating results of behavior modification of the user in response to each advice when the agent presented advices having at least the same higher category a predetermined number of times.

(7)

The information processing system according to any one of (2) to (6), wherein the control unit generates data in which a portion different between a plurality of agents of which at least one of the appearance, voice, and personality of the agent is different from that of the agent is changed continuously, extracts data in the middle of change with an arbitrary number of steps on the generated line of continuous change, and sets the agent in a stepwise manner within the extracted number of steps, and the control unit detects a result of behavior modification of the user when each agent presents advice to the user, and optimizes at least one of the appearance, voice, and personality of the agent on the basis of the detection result.

(8)

The information processing system according to any one of (1) to (7), wherein the control unit sets an initial agent as the user interface of the agent.

(9)

The information processing system according to (8), wherein the control unit sets the user interface of the initial agent according to a profile of the user.

(10)

The information processing system according to (8), wherein the control unit sets a relatively high appearance probability to the user interface of the initial agent, the control unit sets a relatively low appearance probability to user interfaces of agents other than the initial agent, the control unit sets the user interface of the agent according to the appearance probability, and when behavior modification of the user is recognized in response to advice to the user via the set user interface of the agent, the control unit raises the appearance probability of the set user interface of the agent and lowers the appearance probability of the user interfaces of the other agents.

(11)

The information processing system according to any one of (1) to (8), wherein the control unit updates a user interface of an external agent device.

(12)

The information processing system according to (11), wherein the control unit controls an agent device of the user to present advice to the user on the basis of the advice to the user acquired from an external service, and the control unit updates the user interface of the agent device depending on whether the user has performed behavior modification in response to the presented advice.

(13)

An information processing method for causing a processor to execute:

controlling a user interface of an agent to be updated depending on whether a user has performed behavior modification in response to advice that the agent has presented to the user.

(14)

A recording medium having a program recorded thereon, the program causing a computer to function as:

a control unit that controls a user interface of an agent to be updated depending on whether a user has performed behavior modification in response to advice that the agent has presented to the user.

REFERENCE SIGNS LIST

1: Agent device
2: Information processing device
3: Advice service server
4: Sensing device
200: Control unit
201: User information management unit
202: Advice service management unit
203: Initial character determining unit
204: Behavior modification determining unit
205: Character changing unit
210: Communication unit
220: Storage unit
221: User profile DB
222: Private character DB
223: General-purpose character DB

The invention claimed is:

1. An information processing system, comprising:
processing circuitry configured to:
 present N advices within a first time period to a user via a virtual agent user interface using a first virtual agent rendered according to image information of a first agent character selected from an agent character database;
 detect t times of occurrence within the first time period that detected user behaviors of the user follow corresponding ones of the N advices;
 determine whether a ratio t/N is less than a threshold;
 in response to the ratio being determined as less than the threshold, control the virtual agent user interface to be updated to use a second virtual agent within a second time period after the first time period, at least appearance, voice, or personality of the second virtual agent being rendered as different from that of the first virtual agent; and
 in response to the ratio being determined as not less than the threshold, control the virtual agent user interface to keep using the first virtual agent within the second time period.

2. The information processing system according to claim 1, wherein the processing circuitry is further configured to, in response to the ratio being determined as less than the threshold:
 select a second agent character from the agent character database, the second virtual agent being rendered according to image information of the second agent character.

3. The information processing system according to claim 1, wherein the processing circuitry is further configured to, in response to the ratio being determined as less than the threshold:
 control the virtual agent user interface to be updated to use the second virtual agent by adjusting an attribute value of the first agent character with respect to at least one of the appearance, voice, and personality of the first virtual agent.

4. The information processing system according to claim 1, wherein the processing circuitry is further configured to, in response to the ratio being determined as less than the threshold:
 select a second agent character from the agent character database;
 generate M-1 interpolation images by performing interpolation between a first image fully based on the image information of the first agent character and a second image fully based on image information of the second agent character, M-1 being a positive integer, and the M-1 interpolation images showing gradual changes from the first image to the second image; and
 control the virtual agent user interface to be updated to use the second virtual agent based on a first one of the M-1 interpolation images.

5. The information processing system according to claim 4, wherein the processing circuitry is further configured to, after the virtual agent user interface is updated to use the second virtual agent within the second time period based on the first one of the M-1 interpolation images:
 present N' advices within the second time period to the user via the virtual agent user interface using the second virtual agent;
 detect t' times of occurrence within the second time period that detected user behaviors of the user follow corresponding ones of the N' advices;
 determine whether another ratio of t'/N' is less than the threshold; and
 in response to the other ratio being determined as less than the threshold, control the virtual agent user interface to be updated to use a third virtual agent within a third time period after the second time period based on a second one of the M-1 interpolation images.

6. The information processing system according to claim 1, wherein
 the processing circuitry is configured to select an initial agent character from the agent character database to be used by the virtual agent user interface.

7. The information processing system according to claim 6, wherein
 the processing circuitry is configured to select the initial agent character according to a profile of the user.

8. The information processing system according to claim 6, wherein the processing circuitry is configured to:
 in response to a detected user behavior of the user following a corresponding advice presented by the virtual agent user interface using an initial virtual agent rendered according to the initial agent character,
 increase an appearance probability value of the initial agent character, and
 decrease one or more appearance probability values of one or more other agent characters in the agent character database;
 in response to the detected user behavior of the user not following the corresponding advice presented by the virtual agent user interface using the initial virtual agent rendered according to the initial agent character,
 decrease the appearance probability value of the initial agent character, and increase the one or more appearance probability values of the one or more other agent characters in the agent character database; and set the virtual agent user interface according to the appearance probability value of the initial agent character and the one or more appearance probability values of the one or more other agent characters.

9. The information processing system according to claim 1, wherein the processing circuitry is configured to update the virtual agent user interface of an external agent device.

10. The information processing system according to claim 9, wherein the processing circuitry is configured to:

control an agent device of the user to present an advice to the user on a basis of the advice to the user acquired from an external service, and update the virtual agent user interface of the agent device depending on whether the user has performed behavior modification in response to the presented advice.

11. The information processing system according to claim 1, wherein the N advices within the first time period correspond to a same recommendation or one or more different recommendations of a same advice category.

12. An information processing method, comprising:

presenting N advices within a first time period to a user via a virtual agent user interface using a first virtual agent rendered according to image information of a first agent character selected from an agent character database:

detecting t times of occurrence within the first time period that detected user behaviors of the user follow corresponding ones of the N advices:

determining, by processing circuitry of an apparatus, whether a ratio of t/N is less than a threshold:

in response to the ratio being determined as less than the threshold, controlling, by the processing circuitry of the apparatus, the virtual agent user interface to be updated to use a second virtual agent within a second time period after the first time period, at least appearance, voice, or personality of the second virtual agent being rendered as different from that of the first virtual agent, and in response to the ratio being determined as not less than the threshold, controlling the virtual agent user interface to keep using the first virtual agent within the second time period.

13. The information processing method according to claim 12, further comprising, in response to the ratio being determined as less than the threshold:

selecting a second went character from the went character database;

generating M-1 interpolation images by performing interpolation between a first image fully based on the image information of the first agent character and a second image fully based on image information of the second agent character, M-1 being a positive integer, and the M-1 interpolation images showing gradual changes from the first image to the second image; and controlling the virtual agent user interface to be updated to use the second virtual agent based on a first one of the M-1 interpolation images.

14. The information processing method according to claim 13, further comprising, after the virtual agent user interface is updated to use the second virtual agent within the second time period based on the first one of the M-1 interpolation images:

presenting N' advices within the second time period to the user via the virtual agent user interface using the second virtual agent;

detecting t' times of occurrence within the second time period that detected user behaviors of the user follow corresponding ones of the N' advices;

determining whether another ratio of t'/N' is less than the threshold; and in response to the other ratio being determined as less than the threshold, controlling the virtual agent user interface to be updated to use a third virtual agent within a third time period after the second time period based on a second one of the M-1 interpolation images.

15. A non-transitory computer-readable medium having a program recorded thereon, the program when executed by a computer causing the computer to perform a process comprising:

presenting N advices within a first time period to a user via a virtual agent user interface using a first virtual agent rendered according to image information of a first agent character selected from an agent character database;

detecting t times of occurrence within the first time period that detected user behaviors of the user follow corresponding ones of the N advices, determining whether a ratio of t/N is less than a threshold;

in response to the ratio being determined as less than the threshold, controlling the virtual agent user interface to be updated to use a second virtual agent within a second time period after the first time period, at least appearance, voice, or personality of the second virtual agent being rendered as different from that of the first virtual agent; and in response to the ratio being determined as not less than the threshold, controlling the virtual agent user interface to keep using the first virtual agent within the second time period.

16. The non-transitory computer-readable medium according to claim 15, wherein the process further comprises, in response to the ratio being determined as less than the threshold:

selecting a second agent character from the agent character database;

generating M-1 interpolation images by performing interpolation between a first image fully based on the image information of the first agent character and a second image fully based on image information of the second agent character, M-1 being a positive integer, and the M-1 interpolation images showing gradual changes from the first image to the second image; and controlling the virtual agent user interface to be updated to use the second virtual agent based on a first one of the M-1 interpolation images.

17. The non-transitory computer-readable medium according to claim 16, wherein the process further comprises, after the virtual agent user interface is updated to use the second virtual agent within the second time period based on the first one of the M-1 interpolation images:

presenting N' advices within the second time period to the user via the virtual agent user interface using the second virtual agent;

detecting t' times of occurrence within the second time period that detected user behaviors of the user follow corresponding ones of the N' advices;

determining whether another ratio of t'/N' is less than the threshold; and in response to the other ratio being determined as less than the threshold, controlling the virtual agent user interface to be updated to use a third virtual agent within a third time period after the second time period based on a second one of the M-1 interpolation images.

* * * * *